(12) United States Patent
Salzer

(10) Patent No.: US 9,543,117 B2
(45) Date of Patent: Jan. 10, 2017

(54) METHOD OF PROCESSING A MATERIAL-SPECIMEN

(71) Applicant: Carl Zeiss Microscopy GmbH, Jena (DE)

(72) Inventor: Roland Salzer, Leipzig (DE)

(73) Assignee: Carl Zeiss Microscopy GmbH, Jena (DE)

( * ) Notice: Subject to any disclaimer, the term of this patent is extended or adjusted under 35 U.S.C. 154(b) by 448 days.

(21) Appl. No.: 14/077,535

(22) Filed: Nov. 12, 2013

(65) Prior Publication Data
US 2014/0131315 A1 May 15, 2014

(30) Foreign Application Priority Data
Nov. 12, 2012 (DE) .......................... 10 2012 022 168

(51) Int. Cl.
*B44C 1/22* (2006.01)
*H01J 37/305* (2006.01)
*H01L 21/02* (2006.01)
*B23K 26/03* (2006.01)
*B23K 26/14* (2014.01)
*B23K 26/36* (2014.01)
*G01N 1/32* (2006.01)

(52) U.S. Cl.
CPC ........... *H01J 37/3053* (2013.01); *B23K 26/03* (2013.01); *B23K 26/14* (2013.01); *B23K 26/362* (2013.01); *H01J 37/3056* (2013.01); *H01L 21/02* (2013.01); *G01N 1/32* (2013.01); *H01J 2237/3174* (2013.01); *H01J 2237/31744* (2013.01)

(58) Field of Classification Search
CPC ..... B23K 26/03; B23K 26/032; B23K 26/362; B23K 26/126; H01J 2237/3151; H01J 2237/3174
USPC ..................................................... 216/65, 66
See application file for complete search history.

(56) References Cited

U.S. PATENT DOCUMENTS 6,420,703 B1 * 7/2002 Wu .......................... G01N 23/04 250/252.1
2002/0079463 A1 * 6/2002 Shichi ................ B23K 15/0006 250/492.1

(Continued)

OTHER PUBLICATIONS

H. Stegmann et al., "Efficient Target Preparation by Combining Laser Ablation and FIB Milling in a Single Tool", Semiconductor Conference Dresden (SCD), IEEE, 2011, pp. 1-4.

(Continued)

*Primary Examiner* — Binh X Tran
(74) *Attorney, Agent, or Firm* — Fish & Richardson P.C.

(57) ABSTRACT

A method for generating a smooth surface in a material-specimen includes generating a substantially smooth, first surface region by removing a first material-volume by particle beam etching. The first material-volume is partially defined by the first surface region. An angle between a beam direction and a surface normal of the first surface region is greater than 80° and less than 90°. The method also includes generating a substantially smooth, second surface region by removing a second material-volume. The second material-volume is partially defined by the first surface region and is partially defined by the second surface region. An angle between the beam direction and a surface normal of the second surface region is less than 60°.

20 Claims, 3 Drawing Sheets

(56) References Cited

U.S. PATENT DOCUMENTS

2003/0183776 A1* 10/2003 Tomimatsu ............ G01N 1/28
250/442.11
2010/0051828 A1    3/2010  Doemer et al.
2011/0198326 A1    8/2011  Doemer
2013/0323937 A1   12/2013  Kuebler

OTHER PUBLICATIONS

German Office Action, with translation thereof, for corresponding DE Appl No. 10 2012 022 168.1 dated Aug. 6, 2013.
Jon Orloff et al., High Resolution Focused Ion Beams: FIB and Its Applications, Kluwer Academic/Plenum Publishers, NY, Chapter 6.10, pp. 253-254, 2003.

* cited by examiner

METHOD OF PROCESSING A MATERIAL-SPECIMEN

CROSS-REFERENCES TO RELATED APPLICATION

This application claims priority under 35 USC 119 to German Patent Application No. 10 2012 022 168.1, filed Nov. 12, 2012, the entire contents of which are incorporated by reference herein.

FIELD

The present disclosure relates to methods of processing a material-specimen using a particle beam. In particular, the disclosure relates to methods for removing material from the material-specimen by particle beam etching so that a substantially smooth surface region with a small surface roughness is generated on the material-specimen.

BACKGROUND

In the semiconductor industry and other areas of technology, there is a demand for analyzing and/or modifying objects embedded in a volume of a material-specimen such as embedded semiconductor structures or lead layers in a semiconductor element. For example, an electron microscope can be used for analyzing in order to generate an image of the object of interest. As the object of interest is embedded in the material-specimen, the object's surface is exposed by removing a material-volume from the material-specimen before. Background information on such methods of processing may be obtained from, for example, chapter 6.10. of the book "High Resolution Focused Ion Beams: FIB and Its Applications" by Jon Orloff and Mark Utlaut, Kluwer Academic/Plenum Publishers.

The material-volume may be removed precisely by ion beam etching using an ion beam. As the removing of material by ion beam etching is a relatively slow process, at least a portion of the material-volume may also be removed by laser beam processing or by other mechanical or chemical methods. Using laser beam processing and other viable methods, more material-volume per unit time can be removed compared to ion beam etching. However, a surface region having a desired shape can be generated much more precisely by removing material of the material-specimen using ion beam etching than by using laser beam processing and other methods.

It is often desirable to remove material from the material-specimen so that a surface region of the material-specimen is generated which has a substantially smooth shape, i.e. a small roughness.

SUMMARY

The present disclosure is made taking the above considerations into account. Some embodiments of the present disclosure provide a method of processing a material-specimen for removing material from the material-specimen by particle beam etching so that a substantially smooth surface region of the material-specimen is generated.

According to exemplary embodiments, a method of processing a material-specimen includes disposing the material-specimen in a processing region of a particle beam column and orienting the material-specimen relative to the particle beam column in a first orientation; generating a substantially smooth, first surface region of the material-specimen by removing a first material-volume from the material-specimen by particle beam etching using a particle beam generated by the particle beam column, wherein the first material-volume is partially defined by the first surface region and wherein an angle between a beam direction of the particle beam and a surface normal of the first surface region at an intersection of the particle beam and the first surface region is greater than 80° and smaller than 90°; disposing the material-specimen in the processing region of the particle beam column and orienting the material-specimen relative to the particle beam column in a second orientation so that the angle between the beam direction of the particle beam and the surface normal of the first surface region at the intersection of the particle beam and the first surface region is smaller than 70°; and generating a substantially smooth, second surface region of the material-specimen by removing a second material-volume from the material-specimen by particle beam etching using the particle beam generated by the particle beam column, wherein the second material-volume is partially defined by the first surface region and is partially defined by the second surface region and wherein an angle between the beam direction of the particle beam and a surface normal of the second surface region at an intersection of the particle beam and the second surface region is smaller than 60°.

During the generating of the substantially smooth, first surface region, the material-specimen is oriented relative to the particle beam column in the first orientation. Here, the particle beam is incident onto the first surface region at a small angle of less than 10° with respect to the first surface region, i.e. at a large angle of more than 80° with respect to a surface normal of the first surface region at an intersection of the particle beam and the first surface region, and the particle beam may be controlled by controlling deflectors in the particle beam column so that the first surface region is substantially smooth, viewed in a direction transverse to the beam direction of the particle beam. Viewed in direction of the beam direction of the particle beam, the first surface region is also substantially smooth as the particle beam is incident onto the first surface region at the small angle of less than 10° with respect to the first surface region corresponding to a substantially gracing incidence of the particle beam onto the first surface region. Using such a gracing incidence of the particle beam onto the first surface region, bumps or material projections on the first surface region are efficiently removed so that the first surface region may be generated in a simple way so that, there, the surface of the material-specimen is substantially smooth and has a small roughness. Such a substantially gracing incidence of the particle beam onto the first surface region may also be achieved using even smaller angles between the beam direction of the particle beam and the first surface region. This way, this angle may be, for example, less than 6° or less than 3°.

After the generating of the substantially smooth, first surface region, the material-specimen is oriented relative to a particle beam column so that the angle between the beam direction of the particle beam and the first surface region is greater than 20°, i.e. the angle between the beam direction of the particle beam and the surface normal of the first surface region at the intersection of the particle beam and the first surface region is smaller than 70°, and, thus, the particle beam is not incident onto the first surface region at a gracing incidence any more. Using this orientation of the particle beam relative to the first surface region, the ablation rate of material per unit area generated by the particle beam is proportional to the particle dose incident onto the unit area.

Further, the material ablation rate depends only slightly on the orientation of the unit area relative to the direction of the particle beam. If a uniform particle dose is directed onto an area region with a smooth or non-smooth shape of the surface, material is uniformly removed from the surface region so that the shape of the surface of the material-specimen generated after the removing of the material remains unchanged. As the first surface region already has the substantially smooth surface, further surface regions may be generated by directing the particle beam onto the first surface region at non-gracing incidence using particle beam etching which results in a smooth shape of the surface regions. For this, the particle dose per unit area is merely controlled accordingly.

For the second surface region can be, for example, oriented parallel to the first surface region after the removing of the second material-volume, the particle dose per unit area directed onto the material-specimen and projected onto the second area region should be constant across the entire second area region. If it is desired that the second surface region is oriented at a non-vanishing angle to the first surface region, the particle dose directed onto the material-specimen and projected onto the second area region should be chosen to be constant along a direction of a cut between the extrapolated surface of the first surface region and the extrapolated surface of the second surface region and proportionally increases in dependence of the distance to this cut.

Using such controlling of the dose distribution, based on the substantially smooth, first surface region, it is possible to generate the second surface region so that the second surface region is also substantially smooth and has a desired angle relative to the first surface region.

According to further embodiments, the angle between the beam direction of the particle beam and the second surface region is greater than 80° and may be, in particular, 90° or almost 90°, i.e. the angle between the beam direction of the particle beam and the surface normal of the second surface region at the intersection of the particle beam and the second surface region is smaller than 10°, in particular, 0° or almost 0°.

The angle between the first surface region and the second surface region, i.e. the angle between the surface normal at a flat portion of the first surface region and the surface normal of a flat portion of the second surface region may be greater than 20°, greater than 30° or greater than 40°. The angle between the first surface region and the second surface region may also be smaller than 60° and, in particular, smaller than 50°.

According to further embodiments, the method further includes generating a third surface region of the material-specimen by removing a third material-volume from the material-specimen before the disposing of the material-specimen in the processing region of the particle beam column and orienting the material-specimen relative to the particle beam column in the first orientation, wherein the first material-volume is partially defined by the third surface region.

The third material-volume may be removed by a method of processing which may be executed faster or cost less than the particle beam etching so that the generating of the desired, second surface region at a desired location within the original material-specimen is possible faster and cheaper.

The third material-volume may be removed by, for example, laser beam processing from the material-specimen.

Here, it will not be disadvantageous if smooth surfaces with a desired small roughness cannot be generated using the methods of processing chosen for the removing of the third material-volume, as the first surface region generated at gracing incidence of the particle beam has the desired small roughness and the desired second surface region is generated by directing the particle beam onto the first surface region at non-gracing incidence.

Thus, the roughness of the third surface region can be comparatively large and amount to values of 0.5 μm or more, in particular 3 μm or more, while the roughness of the second surface region is significantly smaller and amounts to values of less than 0.2 μm, in particular less than 0.05 μm. Here, the roughness may be determined by, for example, determining the maximum distance measured in direction of a surface normal of the associated surface region between bumps and pits of the surface of the surface region within a square area of side length 10 μm.

Embodiments of the method of processing a material-specimen are illustrated in the following with reference to figures.

BRIEF DESCRIPTION OF THE DRAWINGS

The forgoing as well as other advantageous features of the disclosure will be more apparent from the following detailed description of exemplary embodiments with reference to the accompanying drawings. It is noted that not all possible embodiments necessarily exhibit each and every, or any, of the advantages identified herein.

DETAILED DESCRIPTION OF EXEMPLARY EMBODIMENTS

Figure 1:
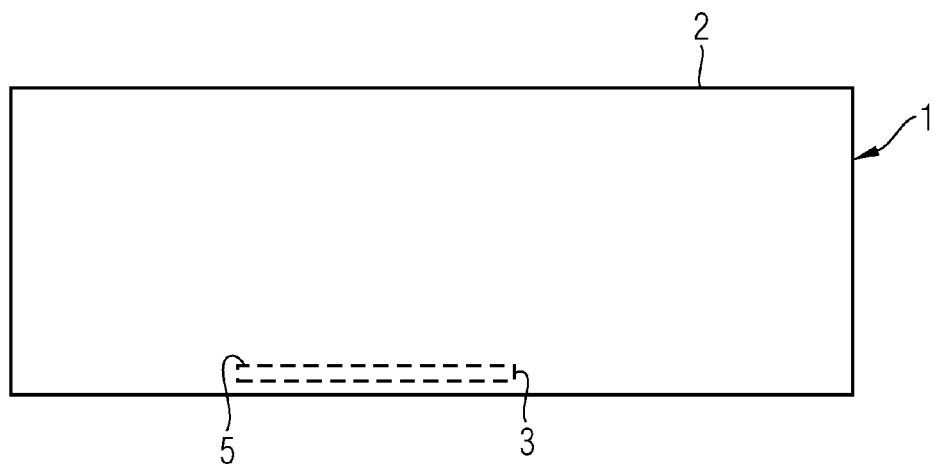
FIGS. 1 to 5 depict cross sections of a material-specimen in multiple consecutive states of a method of processing the material-specimen.

In the exemplary embodiments described below, components that are alike in function and structure are designated as far as possible by alike reference numerals. Therefore, to understand the features of the individual components of a specific embodiment, the descriptions of other embodiments and of the summary of the disclosure should be referred to.

FIG. 1 depicts a cross section of a material-specimen 1 which contains a region of interest 3 to be analyzed, wherein the region of interest 3 has a substantially smooth surface 5, in particular, a flat surface. In order to analyze the region of interest 3 and, in particular, its surface 5, the surface 5 is exposed which involves a removing of a large material-volume from the material-specimen 1. In this embodiment, the region of interest shall be analyzed using an electron microscope, and at least a portion of the material-volume shall be removed by particle beam etching. As the removing of material by particle beam etching is comparatively slow, a relatively large portion of the material-volume shall further be removed by another, quicker kind of processing. In the embodiment described below, laser beam processing is used as the other kind of processing, while ion beam etching is used as the processing by particle beam etching, wherein an ion beam is directed onto the surface of the material-specimen in order to remove material from the material-specimen. Here, a process gas activated by the ion beam or by secondary electrons emerging from the material-specimen due to the ion beam may be supplied to the location of incidence of the ion beam onto the material-specimen, too, in order to react with the material at the surface of the material-specimen and form compounds which dissolve from the surface of the material-specimen.

The processing of the material-specimen and its analysis may be conducted with, for example, a system described in US 2010/0051828 A1 and US 2011/0198326 A1, the disclosures of which are incorporated herein by reference.

Figure 2:
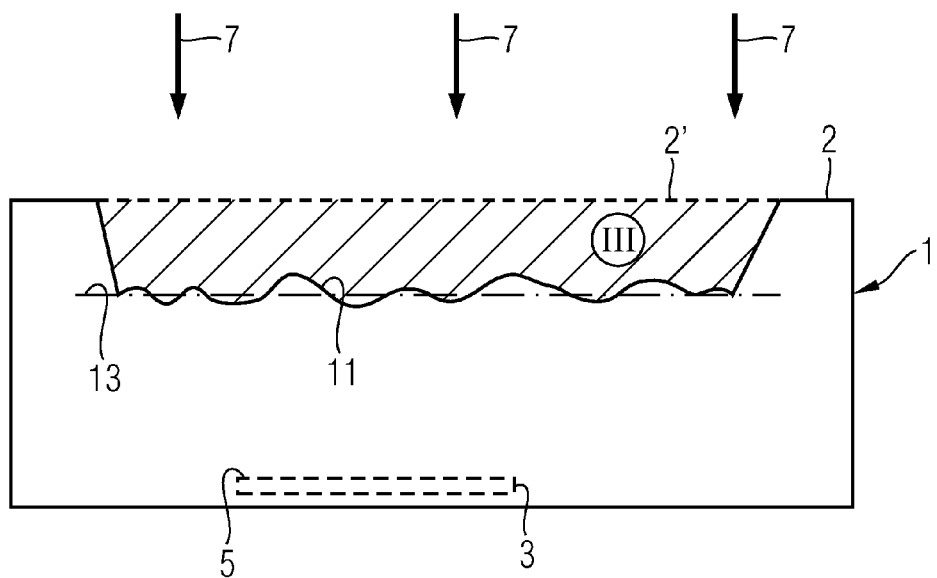

FIG. 2 depicts a cross section of the material-specimen 1 according to FIG. 1 after a first process step. In the first process step, a hatched material-volume labeled III in FIG. 2 is removed from the material-specimen 1. The material-volume III is removed by laser beam processing by directing a laser beam 7 onto the surface 2 of the material-specimen 1. This processing may include the scanning of the laser beam 7 across the material-specimen and a setting of the laser dose per unit area directed onto the material-specimen so that a material-volume is removed from the material-specimen so that a surface region 11 is generated on the material-specimen 1 which is also referred to as a third surface region in the previous description and the position of which is chosen in the material-specimen so that it is advantageous for the following process steps. Here, it is actually desired that the surface region 11 has a substantially smooth surface shape as represented by the dashed line 13 in FIG. 2. However, it is not possible to achieve the desired smooth shape 13 of the surface region 11 by laser beam processing so that the actually generated surface region has a relatively large roughness and deviates from the desired shape 13.

Figure 6:
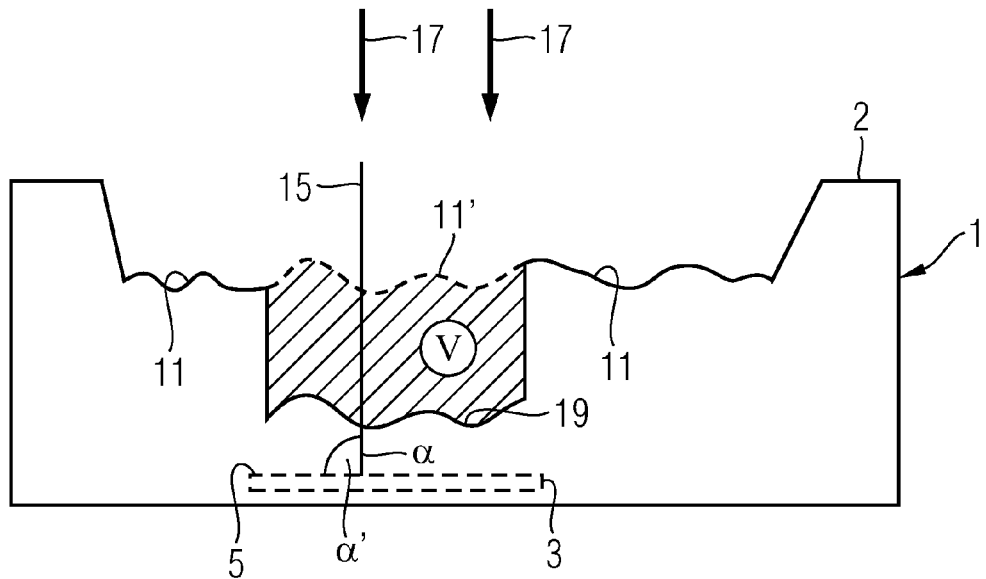
FIG. 6 depicts cross sections of a comparative example of a material-specimen processed according to a conventional method.

FIG. 6 depicts a cross section of the material-specimen 1 after an additional process step commonly used to prepare the surface 5 of the object of interest 3 based on the process step depicted in FIG. 2. Here, after the removing of the material-volume III by laser beam processing according to FIG. 2, an additional material-volume V was removed by ion beam etching. For this, the material-specimen 1 was disposed in a processing region of an ion beam column and oriented so that an angle α' between a beam direction 15 of the ion beam 17 and the surface region 11 substantially amounts to a value of 90°, i.e. an angle α between the beam direction 15 and a surface normal of the surface region 11 at an intersection of the ion beam 17 and the surface region 11 substantially amounts to 0°. The former angle (α') also corresponds to an angle between the beam direction 15 of the ion beam 17 and the surface 5 of the object of interest 3. For removing the material-volume V, the ion beam illustrated by arrows 17 in FIG. 6 is scanned across a partial region of the surface region 11, wherein a same ion dose is directed onto each unit area of this partial region. As the material ablation rate depends only slightly on the orientation of the unit area relative to the ion beam, a same material ablation rate is achieved for each unit area of the partial region so that the surface region 19 generated after the removing of the material-volume V has the same or almost the same surface shape as the portion of the surface region 11 generated by laser beam processing located above, labeled by the numeral 11', as it existed prior to the ion beam etching. Therefore, the shape of the surface region 11 is reproduced by ion beam etching in depth, and it is not possible to generate a substantially smooth surface region 19 by simple ion bean etching, if the original surface region 11, with which the ion beam etching is started with, was not smooth before.

Therefore, the ion beam etching is not performed according to the embodiment of the method described herein with reference to FIG. 6, but a process step is performed by ion beam etching as described below with reference to FIG. 3.

Figure 3:
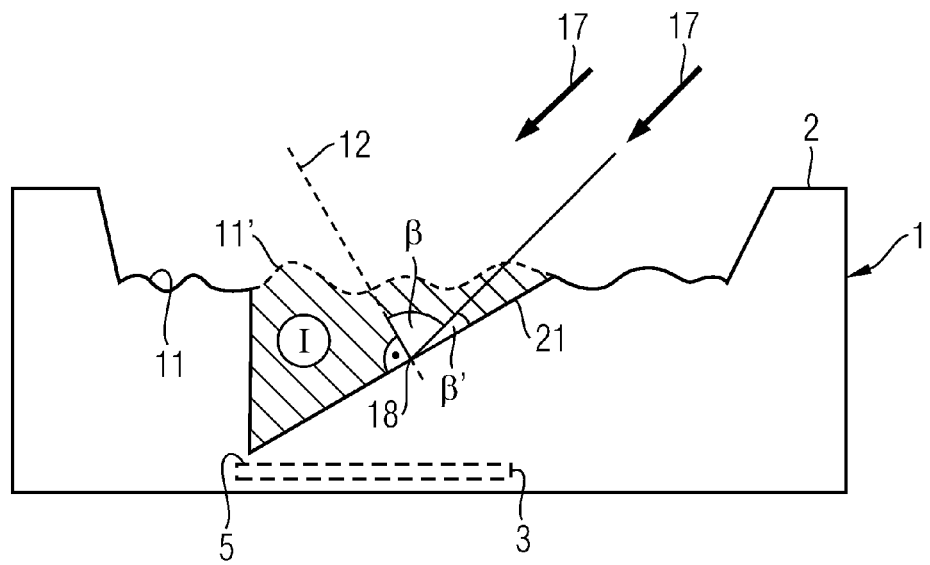

FIG. 3 depicts a cross section of the material-specimen 1 after a process step applied to the material-specimen depicted in FIG. 2. In this process step, a hatched material-volume labeled I was removed from the material-specimen 1. The removing of the material-volume I is performed by ion beam etching by scanning an ion beam represented by arrows 17 across the material-specimen 1 and controlling the ion dose per unit area incident onto the material-specimen 1 so that the removed material-volume I has the desired shape. Thus, a new surface region 21 is generated in the material-specimen 1, wherein the new surface region 21 is also referred to as first surface region in the previous description, and partially defines the material-volume I and has a surface shape which is substantially smooth, i.e. has a comparatively small roughness. This is achieved by orienting the material-specimen 1 relative to the beam direction of the ion beam in a specific way. The beam direction of the ion beam is labeled with the numeral 15 in FIG. 3, the angle between the beam direction 15 of the ion beam 17 and the surface region 21 of the material-specimen 1 is labeled β', and the angle between the beam direction 15 of the ion beam and a surface normal 12 of the surface region 21 of the material-specimen 1 at an intersection 18 of the ion beam 17 and the surface region 21 is labeled β. The value of the angle β' is smaller than 10° and, in particular, smaller than 6°, i.e. the value of the angle β is greater than 80° and, in particular, greater than 84° so that the ion beam 17 is incident onto the surface region 21 at a substantially gracing incidence during the removing of the material-volume I and the generating of the surface region 21. During the gracing incidence of the ion beam onto the surface region 21, bumps and material projections can be efficiently removed by ion beam etching. The generating of the surface region 21 by substantially gracing incidence of the ion beam will result in a substantially smooth surface shape of the surface region 21, if the ion dose is properly controlled. Here, the material-specimen is oriented relative to the ion beam column so that the beam direction of the ion beam is aslant oriented to the surface 5 of the object of interest 3 and, thus, is not orthogonally and not parallelly oriented to that.

After the generating of the surface region 21 according to FIG. 3, the processing is continued with an additional process step described below with reference to FIG. 4.

Figure 4:
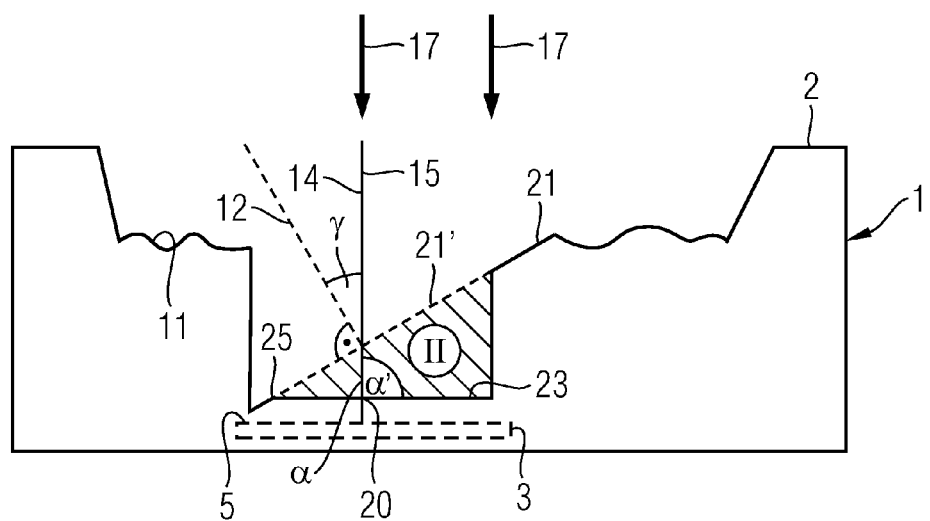

FIG. 4 depicts a cross section of the material-specimen 1 after the removing of the hatched material-volume labeled II in FIG. 4 from the material-specimen 1 after the generating of the surface region 21. Due to the removing of the material-volume II from the material-specimen 1, a surface region 23 partially defining the material-volume II is generated in the material-specimen 1, wherein the surface region 23 was also referred to as second surface region in the previous description. The removing of the material-volume II is performed by ion beam etching, wherein the material-specimen 1 is differently oriented relative to the beam direction 15 of the ion beam as compared to the processing described with reference to FIG. 3. For generating the surface region 23, the material-specimen 1 is oriented relative to the beam direction 15 of the ion beam so that an angle α' between the beam direction 15 and the surface region 23 amounts to a value of exactly or almost 90°, i.e. an angle α between the beam direction 15 and a surface normal 14 of the surface region 23 at an intersection 20 of the ion beam 17 and the surface region 23 amounts to a value of exactly or almost 0°. Thereof deviating angles α' with values greater than 30°, greater than 40°, greater than 50° or greater than 60°, i.e. angles α with values smaller than 60°, smaller than 50°, smaller than 40° or smaller than 30° are also possible. In the illustrated embodiment, the surface region 23 is oriented parallel to the surface 5 of the region of interest 3 and disposed with a small distance from that.

In the illustrated embodiment, the surface region 23 is oriented relative to the surface region 21 at an angle γ represented by an angle between the surface normal 12 of the surface region 21 and the surface normal 14 of the surface region 23. The angle α' between the beam direction 15 of the ion beam and the surface region 23 and, accordingly, the angle α between the beam direction 15 and the surface normal 14 of the surface region 23 at the intersection 20 of the ion beam 15 and the surface region 23 are amounted so that, even when considering the angle γ, the ion beam 17 is incident onto the surface region 21 in a non-gracing incidence during the processing immediately subsequent to the state of the material-specimen according to FIG. 3. In order to avoid the gracing incidence onto the surface region 21, for example, the following condition may hold:

$$\gamma+20°\leq\alpha'\leq90°$$

The position and orientation of the surface region 23 depicted in FIG. 4 may be achieved by ion beam etching based on the surface region 21 illustrated in FIG. 3 by controlling the ion dose per unit area directed onto the material-specimen 1 so that the removed material-volume II has a wedge-like shape. Here, the ion dose projected onto the surface region 23 is controlled so that the ion dose proportionally increases in dependence of the distance from a cut 25 between the surface regions 21 and 23 and is constant along lines which are oriented parallel to the cut 25, i.e. perpendicularly to the plane of projection of FIG. 4. Using this kind of processing by ion beam etching at non-gracing incidence of the ion beam, the surface shape of an initial face, here, of the surface region 21 of FIG. 3, is reproduced as described with reference to FIG. 6. As the initial face 21 has a substantially smooth shape already due to its generating using a substantially gracing incidence of the ion beam, the surface region 23 generated by ion beam etching using non-gracing incidence can have a substantially smooth shape of its surface.

A shape of the surface region 23 is defined by the shape of the removed material-volume II. The shape of the removed material-volume II substantially depends only on the ion dose per unit area directed onto the material-specimen 1 and substantially does not depend on the orientation of the surface region relative to the ion beam. An almost arbitrary shape of the surface region 23 can be achieved by appropriate control of the ion dose per unit area directed onto the material-specimen 1. In the embodiment described with reference to FIG. 4, the surface region 23 is generated as a face parallel to the surface 5 of the object of interest 3. However, it is also possible to generate surface regions which are curved or have a differently shaped desired surface shape while being smooth, i.e. have a small roughness and have only slight deviations with high spatial frequency from the desired surface shape.

At the end of the process step described with reference to FIG. 4, a surface region 23 is generated which is closely disposed to the surface 5 of the object of interest 3 and has a small roughness in its surface so that one can start analyzing the region of interest 3 using an electron microscope or with the help of an ion beam. For this, a focused electron beam or ion beam is scanned across the surface region 23 or a partial region thereof in order to record an electron microscopic or ion microscopic image of the surface region 23. Electrons or ions contribute to the creation of this image which are reflected at the surface of the surface region 23 or in a minor depth of the material underneath the surface as backscattered particles, such as electrons and ions, respectively, or are emanated as secondary electrons.

In the context of this analysis, it is possible to further approach the surface region 23 to the object of interest 3 by additional ion beam etching starting with the orientation of the material-specimen 1 relative to the beam direction of the ion beam illustrated in FIG. 4, as is described below with reference to FIG. 5.

Despite the analysis of the surface region 23 and the object of interest 3, the object of interest 3 can also be modified by ablation of material from the object of interest 3, for example, by particle beam etching or by a particle beam induced deposition of material at the object of interest 3.

Figure 5:
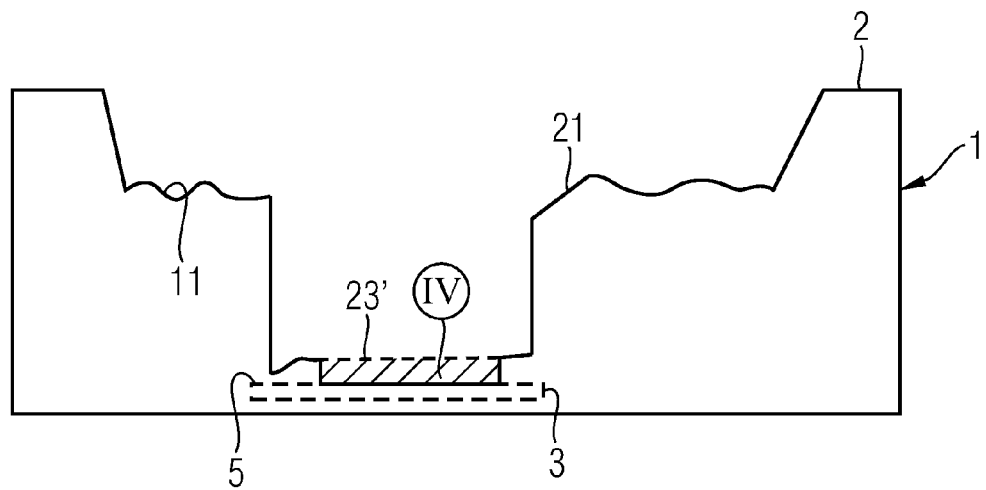

FIG. 5 depicts the material-specimen 1 after a removing of an additional hatched material-volume labeled IV which is generated by controlling the ion dose so that the surface 5 of the object of interest 3 is exposed and can be investigated directly using an electron microscope or an ion microscope. Here, one can proceed step by step: recording an electron microscopic or ion microscopic image of the surface region 23, determining a distribution of the ion dose per unit area at the material-specimen 1 in dependence of the image, performing a step of the ion beam etching according to the determined dose distribution and planning the next step of the ion beam etching again after recording an electron microscopic or ion microscopic image of the then newly generated surface of the portion in order to achieve a precise exposing of the surface 5 of the object of interest 3 without destruction thereof by the ion beam etching.

In addition or alternatively to that, it is also possible to use the electrons and/or ions emerging during the scan-like ablation of the material-volume IV for recording an image of the surface region 23 in order to precisely expose the surface 5.

In addition, it is also possible to monitor all process steps described with reference to FIGS. 1 to 4 using the electron microscope and to control the process steps with it.

The method of processing was described with reference to FIGS. 1 to 6. Each of these figures depicts the cross section of the material-specimen merely schematically, wherein substantially different geometries exist during the processing of the material-specimens in practice. For example, the material-volume III may be substantially larger than the material-volume I or the material-volume II, and the distance between the surface region 2 and the surface region 11 may be substantially larger than the distance between the surface region 11 and the surface region 23, too.

In the previously described embodiment, a method of laser beam processing was used as a fast method of processing for removing the material-volume III which, when used alone, is insufficient to generate a material-surface with the desired small roughness. Instead or in addition to that, another method of processing may be used. Examples of such methods of processing for removing the material-volume III are mechanical methods of processing such as sawing and milling or chemical methods of processing such as etching.

In the previously described embodiment, ion beam etching was further used as the method of processing for removing the material-volume I, the material-volume II and the material-volume IV which allows to generate a material-surface with the desired small roughness. Instead or in addition to that, another method of processing can be used. Examples for such methods of processing for removing the material-volume I, the material-volume II or the material-volume IV are particle beam etching methods such as electron beam etching in conjunction with applying a process gas activated by the electron beam used by the electron beam etching or secondary electrons emerging from the material-specimen due to the electron beam in order to react with the material on the surface of the material-specimen and to form compounds dissolving from the surface of the material-specimen.

Also in the case that an ion beam etching is used as the particle beam etching, a process gas can be applied in addition which is activated by the ion beam or secondary particles emerging from the material-specimen due to the ion beam such as secondary electrons in order to accelerate the material ablation.

While the disclosure has been described with respect to certain exemplary embodiments thereof, it is evident that many alternatives, modifications and variations will be apparent to those skilled in the art. Accordingly, the exemplary embodiments of the disclosure set forth herein are intended to be illustrative and not limiting in any way. Various changes may be made without departing from the spirit and scope of the present disclosure as defined in the following claims.

What is claimed is:

1. A method, comprising:
    disposing a material-specimen in a processing region of a particle beam column and orienting the material-specimen relative to the particle beam column in a first orientation;
    generating a first surface region of the material-specimen by removing a first material-volume from the material-specimen by particle beam etching using a particle beam generated by the particle beam column, the first material-volume being partially defined by the first surface region, and an angle between a beam direction of the particle beam and a surface normal of the first surface region at an intersection of the particle beam and the first surface region being greater than 80° and less than 90°;
    disposing the material-specimen in the processing region of the particle beam column and orienting the material-specimen relative to the particle beam column in a second orientation so that an angle between the beam direction of the particle beam and the surface normal of the first surface region at the intersection of the particle beam and the first surface region is less than 70°; and
    generating a second surface region of the material-specimen by removing a second material-volume from the material-specimen by particle beam etching using the particle beam generated by the particle beam column, the second material-volume being beneath a portion of the first surface region, the second material-volume being partially defined by the second surface region, an angle between the beam direction of the particle beam and a surface normal of the second surface region at an intersection of the particle beam and the second surface region being less than 60°, and the second surface region having a roughness smaller than 0.2 µm.

2. The method of claim 1, wherein the angle between the beam direction of the particle beam and the surface normal of the second surface region at the intersection of the particle beam and the second surface region is less than 10°.

3. The method of claim 1, wherein an angle between a surface normal at a flat portion of the first surface region and a surface normal at a flat portion of the second surface region is greater than 20° and less than 90°.

4. The method of claim 1, wherein an angle between a surface normal at a flat portion of the first surface region and a surface normal at a flat portion of the second surface region is less than 60°.

5. The method of claim 1, wherein the particle beam is an ion beam, the particle beam column is an ion beam column, and the method comprises using ion beam etching to remove at least one material-volume selected from the group consisting of the first material-volume and the second material-volume.

6. The method of claim 1, wherein the particle beam is an electron beam, the particle beam column is an electron beam column, and the method comprises using electron beam etching to remove at least one material-volume selected from the group consisting of the first material-volume and the second material-volume.

7. The method of claim 1, further comprising supplying a process gas to a location of incidence of the particle beam onto the material-specimen when removing at least one material-volume selected from the group consisting of the first material-volume and the second material-volume.

8. The method of claim 1, further comprising, before disposing the material-specimen in the processing region of the particle beam column and orienting the material-specimen relative to the particle beam column in the first orientation, generating a third surface region of the material-specimen by removing a third material-volume from the material-specimen, wherein the first material-volume is partially defined by the third surface region.

9. The method of claim 8, wherein the third material-volume is removed from the material-specimen by laser beam processing.

10. The method of claim 8, wherein the third surface region has a roughness greater than 0.5 µm.

11. A method, comprising:
    generating a first surface region of a material-specimen by removing a first material-volume from the material-specimen by particle beam etching using a particle beam generated by a particle beam column, the first material-volume being partially defined by the first surface region, and an angle between a beam direction of the particle beam and a surface normal of the first surface region at an intersection of the particle beam and the first surface region being greater than 80° and less than 90°;
    orienting the material-specimen relative to the particle beam column in a second orientation so that an angle between the beam direction of the particle beam and the surface normal of the first surface region at the intersection of the particle beam and the first surface region is less than 70°; and
    generating a second surface region of the material-specimen by removing a second material-volume from the material-specimen by particle beam etching using the particle beam generated by the particle beam column, the second material-volume being partially beneath a portion of the first surface region, the second material-volume being partially defined by the second surface region, an angle between the beam direction of the particle beam and a surface normal of the second surface region at an intersection of the particle beam and the second surface region being less than 60°, and the second surface region having a roughness smaller than 0.2 µm.

12. The method of claim 11, wherein the angle between the beam direction of the particle beam and the surface normal of the second surface region at the intersection of the particle beam and the second surface region is less than 10°.

13. The method of claim 11, wherein an angle between a surface normal at a flat portion of the first surface region and a surface normal at a flat portion of the second surface region is greater than 20° and less than 90°.

14. The method of claim 11, wherein an angle between a surface normal at a flat portion of the first surface region and a surface normal at a flat portion of the second surface region is less than 60°.

15. The method of claim 11, further comprising, before disposing the material-specimen in the processing region of the particle beam column and orienting the material-specimen relative to the particle beam column in the first orientation, generating a third surface region of the material-specimen by removing a third material-volume from the material-specimen, wherein the first material-volume is partially defined by the third surface region.

16. The method of claim 11, wherein the particle beam is an ion beam, the particle beam column is an ion beam column, and the method comprises using ion beam etching to remove at least one material-volume selected from the group consisting of the first material-volume and the second material-volume.

17. The method of claim 11, wherein the particle beam is an electron beam, the particle beam column is an electron beam column, and the method comprises using electron beam etching to remove at least one material-volume selected from the group consisting of the first material-volume and the second material-volume.

18. The method of claim 11, further comprising supplying a process gas to a location of incidence of the particle beam onto the material-specimen when removing at least one material-volume selected from the group consisting of the first material-volume and the second material-volume.

19. A method, comprising:
generating a first surface region of a material-specimen by removing a first material-volume from the material-specimen by particle beam etching using a particle beam generated by a particle beam column, the first material-volume being partially defined by the first surface region, and an angle between a beam direction of the particle beam and a surface normal of the first surface region at an intersection of the particle beam and the first surface region being greater than 80° and less than 90°;
orienting the material-specimen relative to the particle beam column in a second orientation so that an angle between the beam direction of the particle beam and the surface normal of the first surface region at the intersection of the particle beam and the first surface region is less than 70°; and
generating a second surface region of the material-specimen by removing material of the material-specimen beneath at least a portion of the first surface region via particle beam etching using the particle beam generated by the particle beam column, an angle between the beam direction of the particle beam and a surface normal of the second surface region at an intersection of the particle beam and the second surface region being less than 60°, the second surface region having a roughness smaller than 0.2 µm.

20. The method of claim 19, wherein the angle between the beam direction of the particle beam and the surface normal of the second surface region at the intersection of the particle beam and the second surface region is less than 10°.

* * * * *